(12) United States Patent
Grote

(10) Patent No.: US 11,202,872 B2
(45) Date of Patent: Dec. 21, 2021

(54) SELECTIVELY ACTIVATE-ABLE HEATING-ELEMENT SYSTEM WITH TWO-OR-MORE HEATING-ELEMENTS

(71) Applicant: Mark James Grote, River Forest, IL (US)

(72) Inventor: Mark James Grote, River Forest, IL (US)

(*) Notice: Subject to any disclaimer, the term of this patent is extended or adjusted under 35 U.S.C. 154(b) by 0 days.

(21) Appl. No.: 16/238,472

(22) Filed: Jan. 2, 2019

(65) Prior Publication Data

US 2020/0205479 A1 Jul. 2, 2020
US 2021/0186119 A9 Jun. 24, 2021

Related U.S. Application Data

(60) Provisional application No. 62/780,755, filed on Dec. 17, 2018, provisional application No. 62/654,187, filed on Apr. 6, 2018.

(51) Int. Cl.
*A61M 15/00* (2006.01)
*A24F 40/46* (2020.01)
*A24F 40/50* (2020.01)

(52) U.S. Cl.
CPC ......... *A61M 15/0001* (2014.02); *A24F 40/46* (2020.01); *A24F 40/50* (2020.01); *A61M 2205/36* (2013.01)

(58) Field of Classification Search
USPC ............................................ 128/202.21, 203
See application file for complete search history.

(56) References Cited

U.S. PATENT DOCUMENTS

| | | | |
|---|---|---|---|
| 7,726,320 B2* | 6/2010 | Robinson | A24B 3/14 131/200 |
| 10,524,518 B1* | 1/2020 | Tygett | A24F 40/50 |
| 10,653,180 B2* | 5/2020 | Monsees | A24F 40/30 |
| 2007/0267031 A1* | 11/2007 | Hon | A24B 15/16 131/273 |
| 2011/0126848 A1* | 6/2011 | Zuber | A24F 40/46 131/329 |
| 2014/0202476 A1* | 7/2014 | Egoyants | A24F 40/46 131/329 |
| 2014/0305449 A1* | 10/2014 | Plojoux | A24F 40/50 131/328 |
| 2015/0013696 A1* | 1/2015 | Plojoux | A61M 15/06 131/328 |

(Continued)

*Primary Examiner* — Nina Bhat
(74) *Attorney, Agent, or Firm* — Robert McConnell; McConnell Law Firm

(57) ABSTRACT

The electronic system for vaporizing smokable materials for personal inhalation includes two or more heating elements for vaporizing *cannabis*, tobacco, e-cigarette fluid and other inhalable materials. Includes a power source and two or more heating elements, each connected to a multi-heating-element circuit-switching-element that allows individual control of the duration and amount of heat applied to each heating element. Each heating element applies heat to one smokable material, which can be contained in a cartridge. The multi-heating-element circuit-switching-element can be a slide switch, push button, rotary encoder, pressure switch, infrared switch, a voice activated switch or a graphical user interface attached to a integrated circuit. The power source can be a battery.

9 Claims, 8 Drawing Sheets

(56) References Cited

U.S. PATENT DOCUMENTS

| | | | |
|---|---|---|---|
| 2015/0313284 A1* | 11/2015 | Liu | A24F 47/008 |
| | | | 131/329 |
| 2016/0106153 A1* | 4/2016 | Zhu | H05B 3/44 |
| | | | 131/329 |
| 2016/0106936 A1* | 4/2016 | Kimmel | A24F 40/51 |
| | | | 128/202.21 |
| 2016/0135505 A1* | 5/2016 | Li | A24F 47/008 |
| | | | 131/329 |
| 2016/0198771 A1* | 7/2016 | Goggin | A24F 40/485 |
| | | | 131/329 |
| 2016/0255878 A1* | 9/2016 | Huang | A61B 5/087 |
| 2017/0295843 A1* | 10/2017 | Storch | A24F 47/008 |
| 2017/0304567 A1* | 10/2017 | Adelson | A61M 11/041 |
| 2018/0263283 A1* | 9/2018 | Popplewell | G05B 13/024 |
| 2019/0104767 A1* | 4/2019 | Hatton | A24F 47/008 |
| 2019/0272359 A1* | 9/2019 | Popplewell | G06F 21/32 |

* cited by examiner

SELECTIVELY ACTIVATE-ABLE HEATING-ELEMENT SYSTEM WITH TWO-OR-MORE HEATING-ELEMENTS

FIELD OF THE INVENTION

The present invention relates to *cannabis*, tobacco, and e-cig inhalation devices for use with their related inhalable substances, such as: fluids, oils, juices, waxes, dabs, shatters, distillates, concentrates, flowers, hashes, tobacco, plant matter, and elements of such nature. The designs herein, offer a *cannabis*, tobacco, and e-cig inhalation user two-or-more selectively activate-able heating-elements for inhaling said *cannabis*, tobacco, and e-cig related substances. Furthermore, the two-or-more selectively activate-able heating-elements offer a user the ability to inhale different types, strains, or flavors of *cannabis*, tobacco, and e-cig substances without the need to reload an inhaling device, physically switch out cartridges or pods, or to have to use two-or-more separate inhaling devices. For the recreational *cannabis*, tobacco, and e-cig industries this merely offers a luxury and new spectrum of ways to inhale substances, but for the medical *cannabis* industry this offers users who require two-or-more strains of medical *cannabis* throughout the day or blends of two-or-more substances for medical reasons, the benefit and convenience of using only one device and not having to reload it every time they need to switch strains.

BACKGROUND OF THE INVENTION

*Cannabis*, tobacco, and e-cig inhalation devices have been around for a long time but have always been focused around the act of inhaling 1 type of *cannabis*, tobacco, or e-cig substances at a time. The aforementioned causes a user to have to install different flavors or strains of these substances into an inhalation device 1 at a time while having to wait to load any new inhalable content into the device until it has been inhaled and depleted by the user, or until a user physically wants to switch out a given substance with a different one due to boredom, taste, or medical needs. The aforementioned further causes a user to have to carry on them multiple inhalation devices or multiple cartridges, pods, or other styles of substance-filled or substance fillable atomizer cavities or chambers for their needs or desires throughout any given day, in terms of portable inhalation devices.

The selectively activate-able heating-elements system with two-or-more heating-elements devised herein, may be fabricated to fit into any designable *cannabis*, tobacco, or e-cig inhalation device housing. This can be done in a plurality of ways that will allow any user to pre-load two-or-more types of *cannabis* substances, tobacco substances, e-cig substances, or any combination thereof into their inhalation devices and inhale them selectively, via user input with a circuit-switching-element

SUMMARY

As such, there is a need for a circuit-switching-element and therefore a selectively activate-able heating-elements system with two-or-more heating-elements, of which different designs could comprise a plurality of methods for activating multiple heating-elements in various ways. The present invention is directed toward solutions to address the needs of different medical *cannabis* patients and recreational *cannabis*, tobacco and e-cig inhalation device users.

According to a first aspect of the invention, a selectively activate-able heating-element system with two-or-more heating-elements includes: Two-or-more heating-elements, separate substance-fillable cavities for each existing heating-element that further houses their each existing heating-elements, a circuit-switching-element, an electric power source, and electrical pathways connecting the aforementioned components in an operable fashion. Any heating-element in a common design includes a short and thin resistive wire wound into a series of coils who's center diameter[s] is typically 2-4 mm and who's total length is approximately 4 mm however these can be much longer and thicker in e-cig inhalation devices as opposed to *cannabis* inhalation devices. Said coils' resistance is typically within a range of 0.2 and 8 ohms with most modern designs and can be comprised of various materials such as nichromes, stainless steels, nickels, or titanium's. Some examples of said circuit-switching-elements are: a 2-way switch, a 3-way switch, a 10 way switch, 2 or more momentary push buttons electrically connected to their own dedicated heating elements separately or in various combinations, a rotary encoder, a pressure switch, a heat activated switch, an infra red switch, a voice activated switch, a graphical user interface (GUI) in conjunction with an integrated circuit (IC), or any other various types of circuit-switching-elements Said power source is a re-chargeable battery in the case of portable inhalation devices or a plug for connecting to a standard 110 v or 220 v wall outlet for not portable inhalation devices, however it could also be comprised of disposable batteries, solar cells, or more uncommon methods. Said electrical pathways connecting all the components in an operable fashion are either wires, traces on (PCB's) Printed Circuit Boards, or metal body of any given metal inhalation device acting as a common ground that other wires, contacts or PCB circuits may connect with.

In accordance with one specific implementation, the system includes 3 heating-elements individually composed of a 1 inch long piece of 316 SS Wire that is 2.4 ohms (stainless steel) and is 26 AWG (approximate diameter is 0.0159"). The wire is wound into 3-4 coils that are approximately 2 mm in diameter each, leaving the coils overall length to be roughly 4 mm long with its extra lengths protruding down on each side so that they may be connected to the rest of the system. Next, an SP3T (Single Pole 3 Throw) electrical switch that can handle 5 volts will act as said circuit-switching-element. Said SP3T switch will allow for the switching of the distribution of power between the 3 heating-elements. Next, 1 end of each wire of 3 separate insulated wires (copper or aluminum wires) that are approximately 3 inches long each will each be dedicated to their own electrical terminal on said SP3T switch for receiving distributable power from said electronic power source. Note: 1 of the 4 terminals on the SP3T switch is dedicated for the positive terminal of the power source for receiving power. Next, the free end of each wire connected to said SP3T switch will be arbitrarily connected to 1 of the 2 legs of its own dedicated heating-element, of each one of said 3 available heating-elements. Next a 3.8-4.2 volt battery is connected to said power receiving terminal on said SP3T switch to complete and observe a functional circuit. Said battery is then inserted into an appropriate battery holder that will have a positive and negative (ground) wire coming off of it setup to make good contact with the corresponding terminals of said battery. Another insulated wire roughly 3 inches long then connects to the available power receiving terminal on said SP3T switch and its other end then connects to the positive terminal on the battery holder. Lastly, 3 new wires connect each free terminal of each said heating-element to the negative battery terminal via the negative or ground battery holder wire. The circuit is now complete, and the circuit-switching-element can be switched to any of its 3 positions in order to activate any 1 heating element independently of the others, each remaining deactivated unless switched to. Further note, an SP4T switch could be used in place of an SP3T switch so that the switch can have 1 terminal that nothing is connected to, as to be used as an OFF position for electric current from said electric-power-source. Furthermore, a normally open momentary push button could be added between the power source and switch on the positive wire connecting them, in order to keep the heating elements deactivated unless the momentary push button is pressed and held down. There are a plurality of ways that a safety measure of keeping the power disconnected from the heating-elements when not in use, could be achieved. There are also a plurality of different parts, buttons, switches, power sources, and wires that could be used to achieve different designs, looks, and user interactions for said electronic system described herein.

BRIEF DESCRIPTION OF THE FIGURES

The present invention will be described in detail with reference to the figures, in which numerals and alphanumerics indicate like references in the description. These and other features will be better understood, in which:

FIGS. 13 and 14 comprise the four core novel elements of the invention and are direct evolutions of FIG. 2.

Furthermore, the two independent pushbuttons in this depiction are connected to the heating-elements in such a way as to allow a 1st heating-element to be activated independently or a $2^{nd}$ and $3^{rd}$ heating-element to be activated in tandem. This depicts the This depicts the diverse applications of circuit-switching-elements within the innovated circuit herein

FIG. 9, further depicts a press-fit style electrical contact system for connecting said heating-elements to said circuit-switching-element, similar to that of many fluorescent light bulbs. This represents an embodiment of said heating-elements as being part of a $3^{rd}$ party component like a *cannabis* or e-cig substance cartridge or pod.

FIG. 12 further depicts a (GUI) Graphical User Interface being operably connected to an (IC) Integrated Circuit which is acting as said circuit-switching-element, in tandem with said GUI.

FIG. 13, depicts a diagrammatic view of a system in which two-or-more heating-elements are interfaced with a circuit-switching-element and an electric power source, in such a way that their heating abilities may be selectively activated or deactivated by means of user interaction with said circuit-switching-element. Further depicted are separate substance-fillable cavities each housing their own said heating-elements.

FIG. 14, depicts a diagrammatic view of the same system of FIG. 13 in which two-or-more heating-elements are interfaced with a circuit-switching-element and an electric power source, in such a way that their heating abilities may be selectively activated or deactivated by means of user interaction with said circuit-switching-element.

Further depicted are separate substance-fillable cavities each housing their own said heating-elements. Lastly, a shared cavity housing is depicted wherein the two substance-finable cavities are a part of the same material or are unified with an aggregate housing.

DETAILED DESCRIPTION

Figure 1:
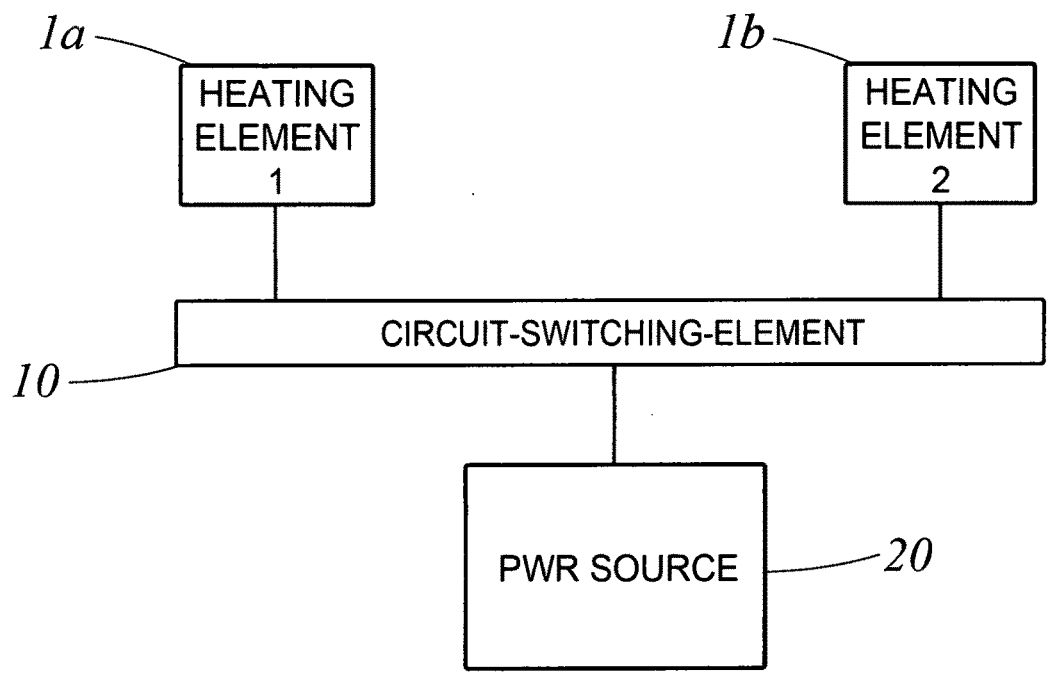
FIG. 1, depicts a diagrammatic view of a system in which two-or-more heating-elements are interfaced with a circuit-switching-element and an electric power source, in such a way that their heating abilities may be selectively activated or deactivated by means of user interaction with said circuit-switching-element.
Figure 13:
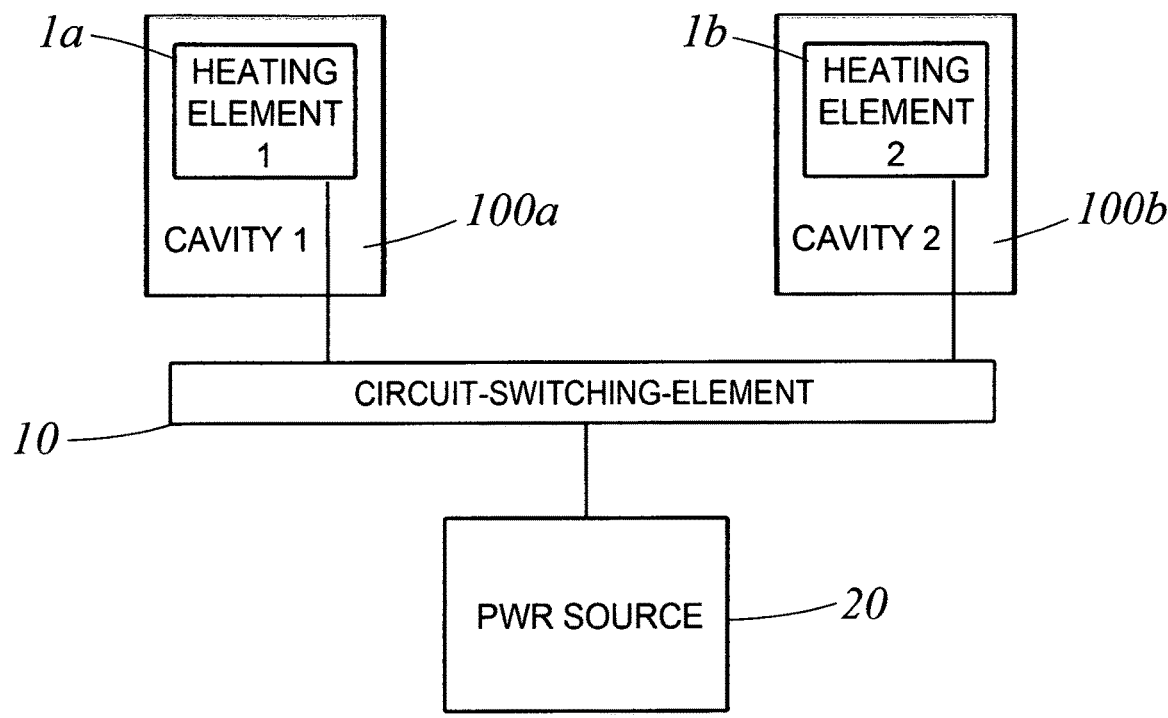
FIGS. 13 and 14 comprise the 4 core novel elements of the invention and are direct evolutions of FIG. 1.
Figure 14:
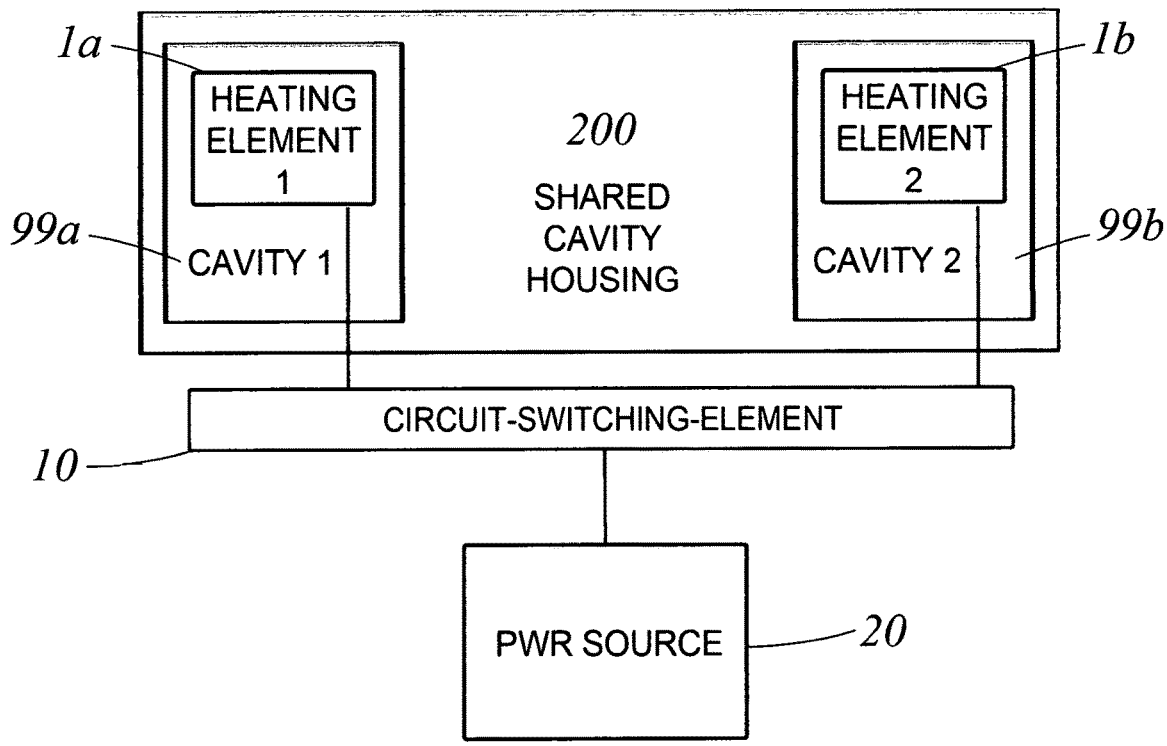

The present invention will be described in detail with reference to the figures, in which numerals and alphanumerics indicate like references in the description. These and other features will be better understood, in which:

FIG. 1, depicts a diagrammatic view of a system in which two-or-more heating-elements $1a$, $1b$ are interfaced with a circuit-switching-element 10 and an electric power source 20, in such a way that their heating abilities may be selectively activated or deactivated by means of user interaction with said circuit-switching-element 10. FIGS. 13 and 14 comprise the four core novel elements of the invention and are direct evolutions of FIG. 1.

Figure 2:
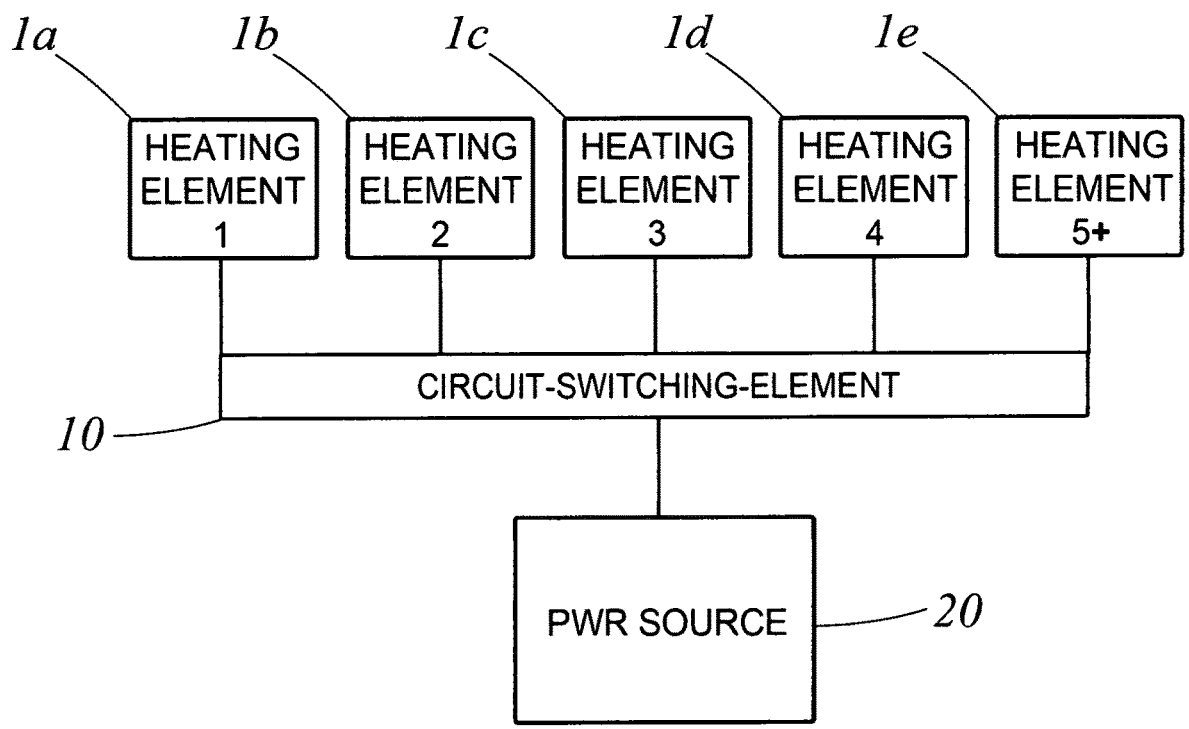
FIG. 2, depicts a diagrammatic view of a system in which two-or-more heating-elements are interfaced with a circuit-switching-element and an electric power source, in such a way that their heating abilities may be selectively activated or deactivated by means of user interaction with said circuit-switching-element.

FIG. 2, depicts a diagrammatic view of a system in which two-or-more heating-elements $1a$, $1b$, $1c$, $1d$, $1e$ are interfaced with a circuit-switching-element 10 and an electric power source 20, in such a way that their heating abilities may be selectively activated or deactivated by means of user interaction with said circuit-switching-element 10. FIGS. 13 and 14 comprise the 4 core novel elements of the invention and are direct evolutions of FIG. 2.

Figure 3:
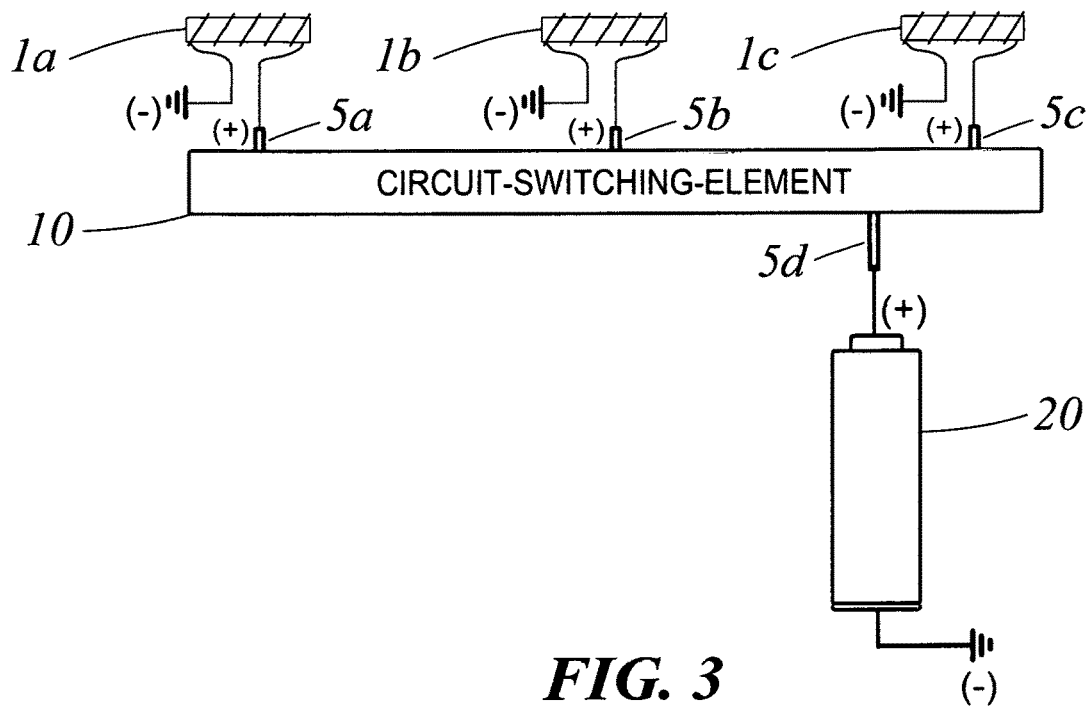
FIG. 3, depicts a system in which two-or-more heating-elements are interfaced with a circuit-switching-element and an electric power source, in such a way that their heating abilities may be selectively activated or deactivated by means of user interaction with said circuit-switching-element. Furthermore, it depicts an electric power source as being a battery.

FIG. 3, depicts a system in which two-or-more heating-elements $1a$, $1b$, $1c$ are interfaced with a circuit-switching-element 10 and an electric power source 20, in such a way that their heating abilities may be selectively activated or deactivated by means of user interaction with said circuit-switching-element 10. Furthermore, it depicts an electric power source 20 as being a battery 20. It further depicts said two-or-more heating-elements $1a$, $1b$, $1c$ being interfaced to said circuit-switching-element 10 by being connected to the positive output electrodes $5a$, $5b$, $5c$ of said circuit-switching-element 10. Lastly, the battery 20 is also connected to said circuit-switching-element 10 by being connected to the positive input electrode $5d$ of said circuit-switching-element 10.

Figure 4:
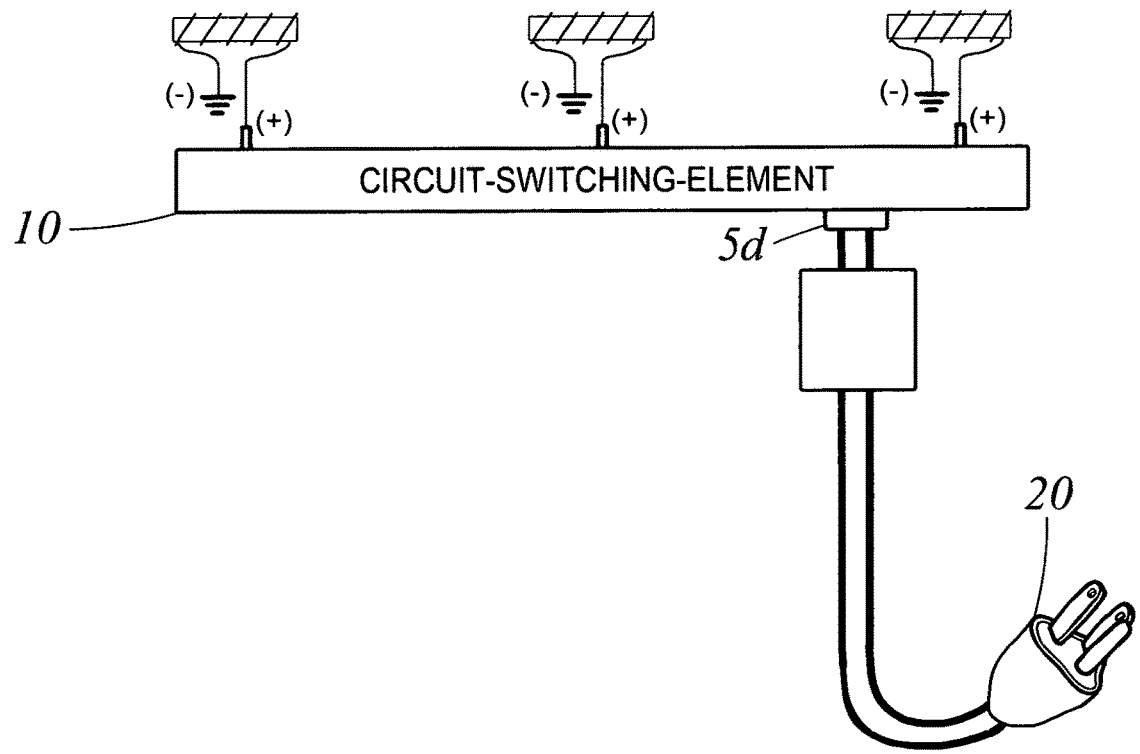
FIG. 4, depicts a system in which two-or-more heating-elements are interfaced with a circuit-switching-element and an electric power source, in such a way that their heating abilities may be selectively activated or deactivated by means of user interaction with said circuit-switching-element. Furthermore, it depicts an electric power source as being a wall plug for connecting to a standard 110 v wall socket.

FIG. 4, depicts a system in which two-or-more heating-elements are interfaced with a circuit-switching-element 10 and an electric power source 20, in such a way that their heating abilities may be selectively activated or deactivated by means of user interaction with said circuit-switching-element 10. Furthermore, it depicts an electric power source as being a wall plug for connecting to a standard 110 v wall socket. Lastly, said electric power source 20 is also connected to said circuit-switching-element 10 by being connected to the positive input electrode $5d$ of said circuit-switching-element 10 with its positive terminal. The groundside of each heating-element would then connect to the negative terminal of the power source 20.

Figure 5:
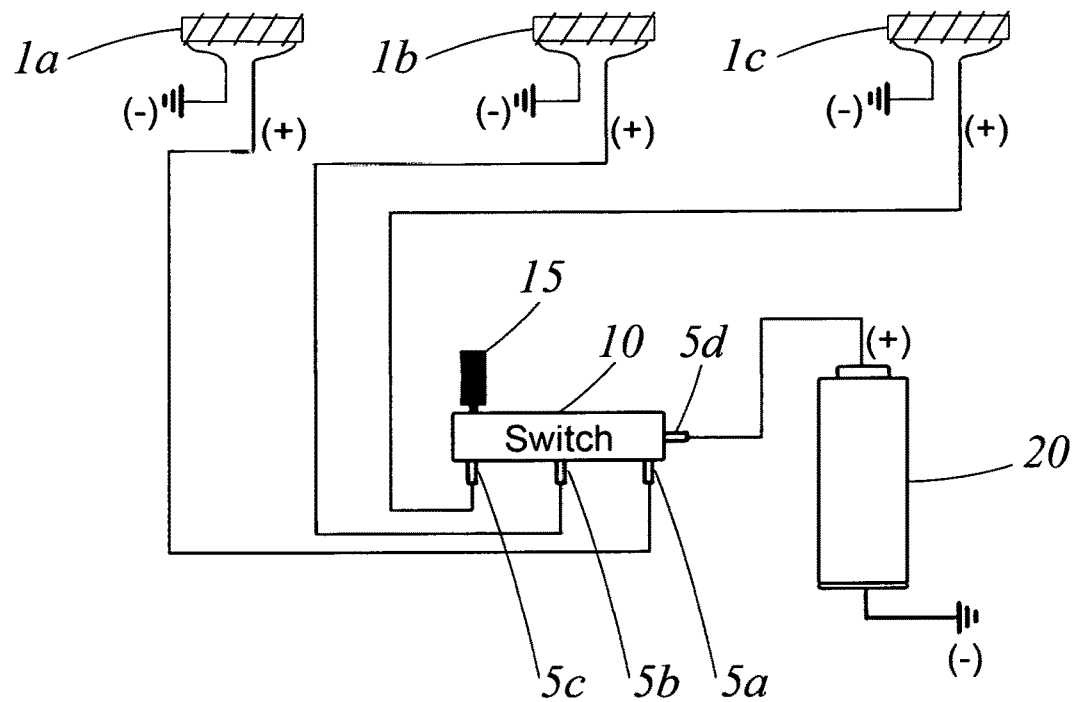
FIG. 5, depicts a system in which two-or-more heating-elements are interfaced with a circuit-switching-element and electric power source, in such a way that their heating abilities may be selectively activated or deactivated by means of user interaction with said circuit-switching-element. In this depiction, an SP3T or 3-way electronic switch comprising a user-interactive slide-knob is functioning as said circuit-switching-element.

FIG. 5, depicts a system in which two-or-more heating-elements $1a$, $1b$, $1c$ are interfaced with a circuit-switching-element 10 and electric power source 20, in such a way that their heating abilities may be selectively activated or deactivated by means of user interaction with said circuit-switching-element 10. In this depiction, an SP3T or 3-way electronic 10 switch comprising a user-interactive slide-knob 15 is functioning as said circuit-switching-element 10. Furthermore, the battery 20 is also connected to said circuit-switching-element 10 by being connected to the positive input electrode $5d$ of said circuit-switching-element 10. Further observe, that a $1^{st}$ heating-element $1a$ is connected to a $1^{st}$ positive output electrode $5a$ of said circuit-switching-element 10. Additionally, a $2^{nd}$ heating-element $1b$ is connected to a $2^{nd}$ positive output electrode $5b$ and lastly a $3^{rd}$ heating-element $1c$ is connected to a $3^{rd}$ positive output electrode $5c$. The setup described herein, is one of many means in which a circuit-switching-element 10 may be interfaced to selectively distribute power to two-or-more heating-elements $1a$, $1b$, $1c$ by the act of switching between them, in this example with a slide-knob 15.

Figure 6:
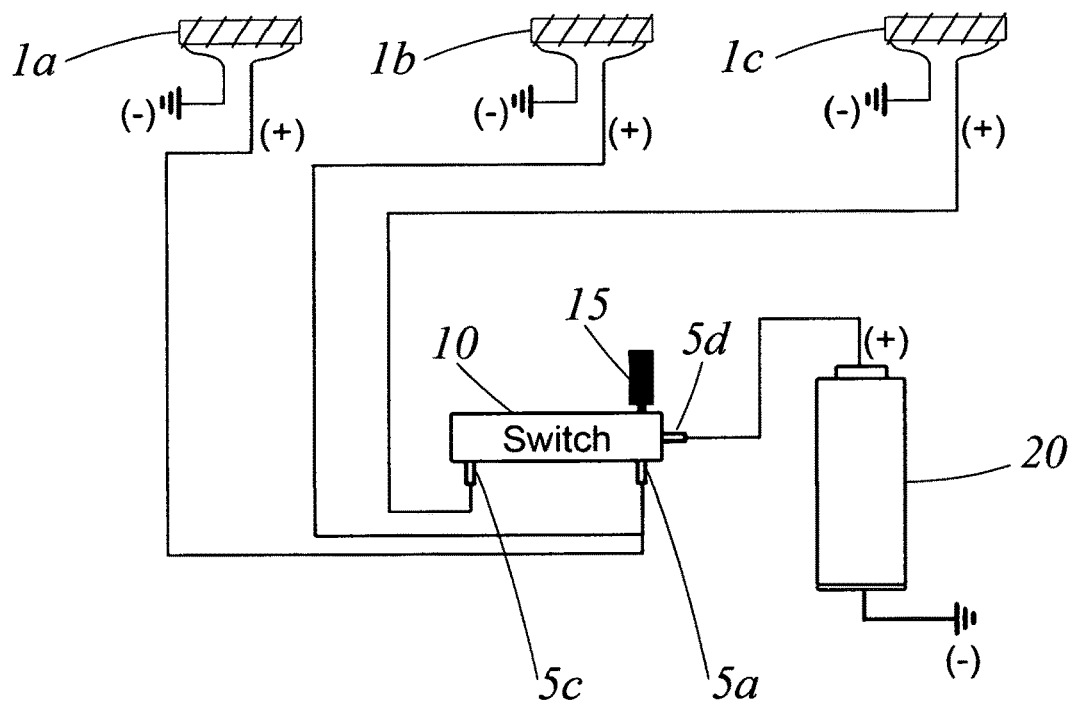
FIG. 6, depicts a system in which two-or-more heating-elements are interfaced with a circuit-switching-element and electric power source, in such a way that their heating abilities may be selectively activated or deactivated by means of user interaction with said circuit-switching-element. In this depiction, an SP2T or 2-way electronic switch comprising a user-interactive slide-knob is functioning as said circuit-switching-element. Furthermore, the 2-way electronic switch in this depiction is connected to the two-or-more heating-elements in such a way as to allow a 1st heating-element to be activated independently or a $2^{nd}$ and $3^{rd}$ heating-element to be activated in tandem. This depicts the diverse applications of circuit-switching-elements within the innovated circuit herein.

FIG. 6, depicts a system in which two-or-more heating-elements $1a$, $1b$, $1c$ are interfaced with a circuit-switching-element 10 and electric power source 20, in such a way that their heating abilities may be selectively activated or deactivated by means of user interaction with said circuit-switching-element 10. In this depiction, an SP2T or 2-way electronic switch 10 comprising a user-interactive slide-knob 15 is functioning as said circuit-switching-element 10. Furthermore, said 2-way electronic switch 10 in this depiction is connected to the two-or-more heating-elements $1a$, $1b$, $1c$ in such a way as to allow a 1st heating-element $1a$ to be activated independently or a $2^{nd}$ and $3^{rd}$ heating-element $1b$, $1c$ to be activated in tandem. This depicts the diverse uses of circuit-switching-elements 10 within the innovated circuit herein. Furthermore, said battery 20 is also connected to said circuit-switching-element 10 by being connected to the positive input electrode $5d$ of said circuit-switching-element 10. Further observe, that a $1^{st}$ and $2^{nd}$ heating-element $1a$, $1b$ are collectively connected to a $1^{st}$ positive output electrode $5a$ of said circuit-switching-element 10 so said heating-elements can be activated at the same time. If said heating-elements $1a$, $1b$, $1c$ were housed in separate substance-filled cavities $100a$, $100b$, $100c$ of FIG. 10 or $100a$, $100b$ of FIG. 13 or $99a$, $99b$, $99c$ of FIG. 11 or FIG. 12 or $99a$, $99b$ of FIG. 14 this would allow a user to mix the substances when inhaled. Additionally, a $3^{rd}$ heating-element $1c$ is connected to a $2^{nd}$ positive output electrode $5c$, if this $3^{rd}$ heating-element $1c$ was also housed in a separate substance-filled cavity it would then offer a $3^{rd}$ flavor or strain of a substance that could be inhaled by a user, separately from the other two heating-elements $1a$, $1b$. The setup described herein, is one of many means in which a circuit-switching-element 10 may be interfaced to selectively distribute power to two-or-more heating-elements $1a$, $1b$, $1c$ by the act of electronically switching between them, further implemented in this example with a slide-knob 15.

Figure 7:
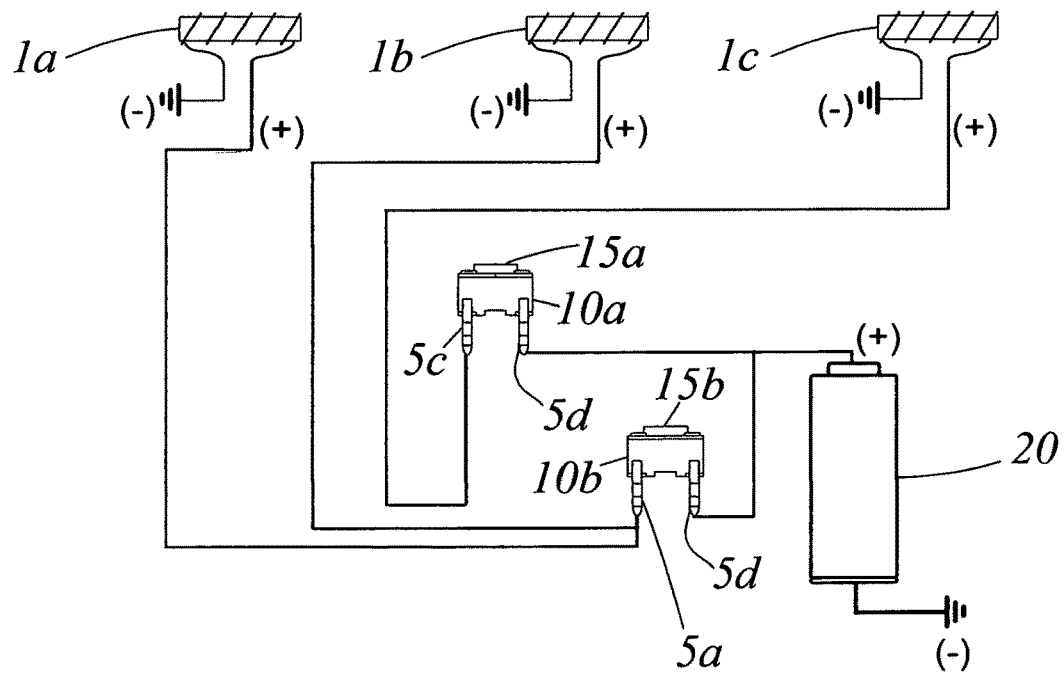
FIG. 7, depicts a system in which two-or-more heating-elements are interfaced with a circuit-switching-element and electric power source, in such a way that their heating abilities may be selectively activated or deactivated by means of user interaction with said circuit-switching-element. In this depiction, two separated and normally-open momentary pushbuttons are functioning collectively as said circuit-switching-element.

FIG. 7, depicts a system in which two-or-more $1a$, $1b$, $1c$ heating-elements are interfaced with a circuit-switching-element $10a$, $10b$ and electric power source 20, in such a way that their heating abilities may be selectively activated or deactivated by means of user interaction with said circuit-switching-element 10a, 10b. In this depiction, two separated and normally-open momentary pushbuttons 10a, 10b are functioning collectively as said circuit-switching-element 10a, 10b. Furthermore, the two independent pushbuttons 10a, 10b in this depiction are connected to the heating-elements 1a, 1b, 1c in such a way as to allow a 1st heating-element 1c to be activated independently or a $2^{nd}$ and $3^{rd}$ heating-element 1a, 1b to be activated in tandem. This depicts the diverse applications of circuit-switching-elements within the innovated circuit herein. Furthermore, the battery 20 is also connected to said circuit-switching-element 10a, 10b by being connected to the positive input electrode 5d of said circuit-switching-element 10a, 10b. Further observe, that a $1^{st}$ and $2^{nd}$ heating-element 1a, 1b are collectively connected to a $1^{st}$ positive output electrode 5a of said circuit-switching-element['] 10a, 10b. Notice how the collective fastening of the electrode 5a to said heating-elements' 1a, 1b positive electrodes would activate both heating-elements 1a, 1b at the same time upon pressing and holding down on the button 15b of the normally-open momentary push button 15b, thus depicting how said circuit-switching-elements 10a, 10b can heat two-or-more heating-elements 1a, 1b at once. Additionally, a $3^{rd}$ heating-element 1c is connected to a $2^{nd}$ positive output electrode 5c on circuit-switching-element 10a. The setup described herein, is one of many means in which a circuit-switching-element 10a, 10b may be used to selectively distribute power to two-or-more heating-elements 1a, 1b, 1c. In this example, this is achieved by the act of pressing and holding down either of the normally-open momentary push buttons 15a, 15b. If said heating-elements 1a, 1b, 1c were housed in separate substance-filled cavities 100a, 100b, 100c of FIG. 10 or 100a, 100b of FIG. 13 or 99a, 99b, 99c of FIG. 11 or FIG. 12 or 99a, 99b of FIG. 14 this would allow a user to mix the substances when inhaled.

Figure 8:
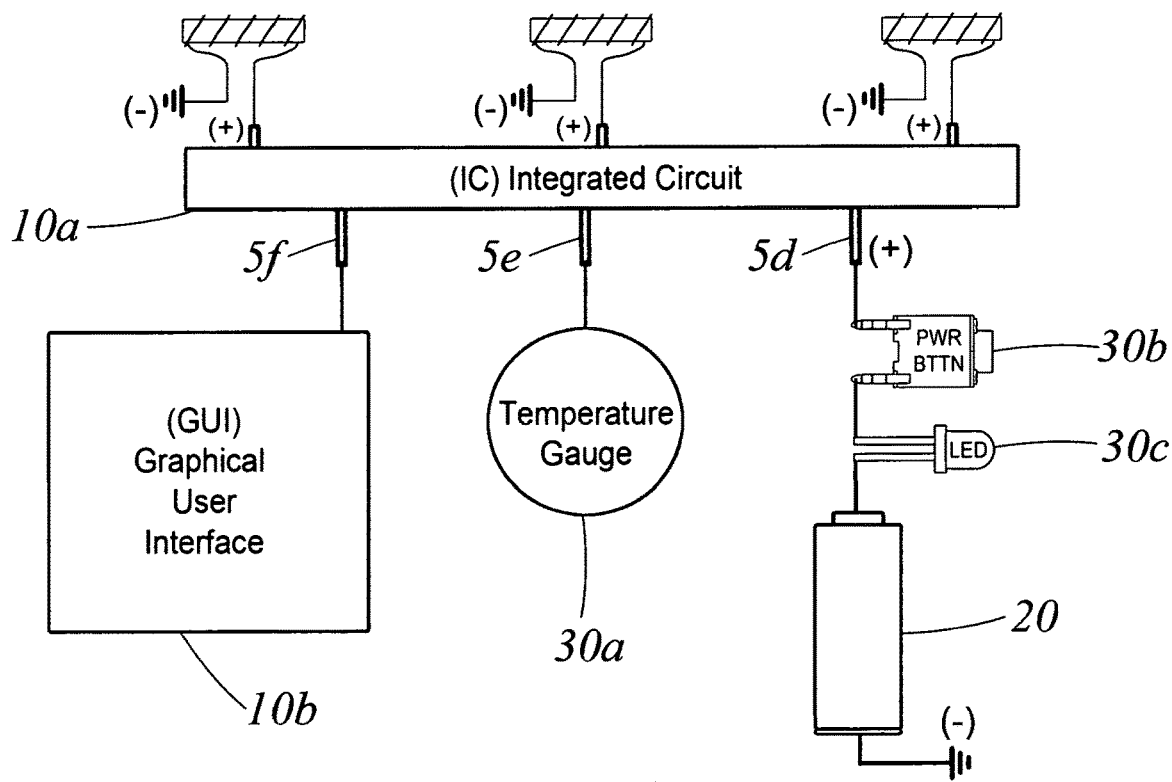
FIG. 8, depicts a system in which two-or-more heating-elements are interfaced with a circuit-switching-element and electric power source, in such a way that their heating abilities may be selectively activated or deactivated by means of user interaction with said circuit-switching-element. In this case said circuit-switching-element is an Integrated Circuit (IC). The IC is further connected to a Graphical User Interface (GUI), temperature gauge, hybrid power and inhalation activation button, L.E.D. power indicator, and power source. These extra components are benefits that can be added to the invented circuit herein.

FIG. 8, depicts a system in which two-or-more heating-elements are interfaced with a circuit-switching-element 10a, 10b and electric power source 20, in such a way that their heating abilities may be selectively activated or deactivated by means of user interaction with said circuit-switching-element 10a, 10b. In this case said circuit-switching-element 10a, 10b is an Integrated Circuit (IC) 10a that is interfaced to a Graphical User Interface (GUI) 10b. The GUI 10b is further interfaced to a temperature gauge 30a, hybrid power and inhalation activation button 30b, L.E.D. power indicator 30c, and electric power source 20. Many of these components are extra benefits that can be added to the invented circuit herein. Further more the GUI 10b is represented as being connected to the IC 10a by terminal 5f. Further more the temperature gauge 30a is represented as being connected to the IC 10a by terminal 5e. Further more said electric power source 20, L.E.D. 30c, and said hybrid power and inhalation activation button 30b are represented as being connected to the IC 10a by terminal 5d.

Figure 9:
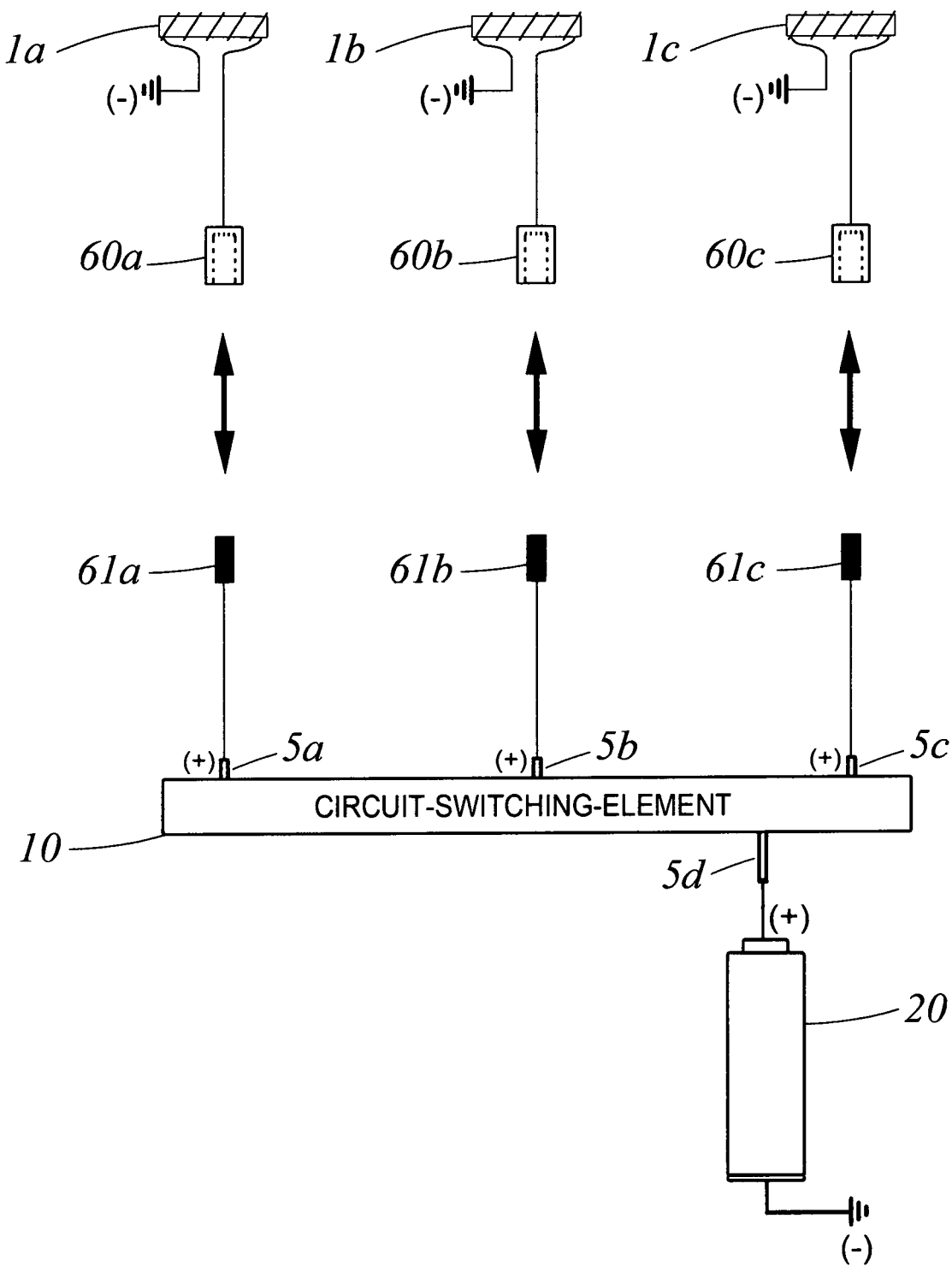
FIG. 9, depicts a system in which two-or-more heating-elements are interfaced with a circuit-switching-element and electric power source, in such a way that their heating abilities may be selectively activated or deactivated by means of user interaction with said circuit-switching-element.

FIG. 9, depicts a system in which two-or-more heating-elements 1a, 1b, 1c are interfaced with a circuit-switching-element 10 and electric power source 20, in such a way that their heating abilities may be selectively activated or deactivated by means of user interaction with said circuit-switching-element 10. FIG. 9, further depicts a press-fit style electrical contact system 60a, 61a, 60b, 61b, 60c, 61c for connecting said heating-elements to said circuit-switching-element 10, similar to that of many fluorescent light bulbs. Furthermore, the battery 20 is also connected to said circuit-switching-element 10 by being connected to the positive input electrode 5d of said circuit-switching-element 10. The male press-fit style electrodes 61a, 61b, 61c, are connected to said circuit-switching-element 10 by positive output electrodes 5a, 5b, and 5c. The female press-fit style electrodes 60a, 60b, 60c, are connected to the heating-elements 1a, 1b, 1c. The female press-fit style electrodes 60a, 60b, 60c, would be inserted into their respective male counterparts 61a, 61b, 61c.

Figure 10:
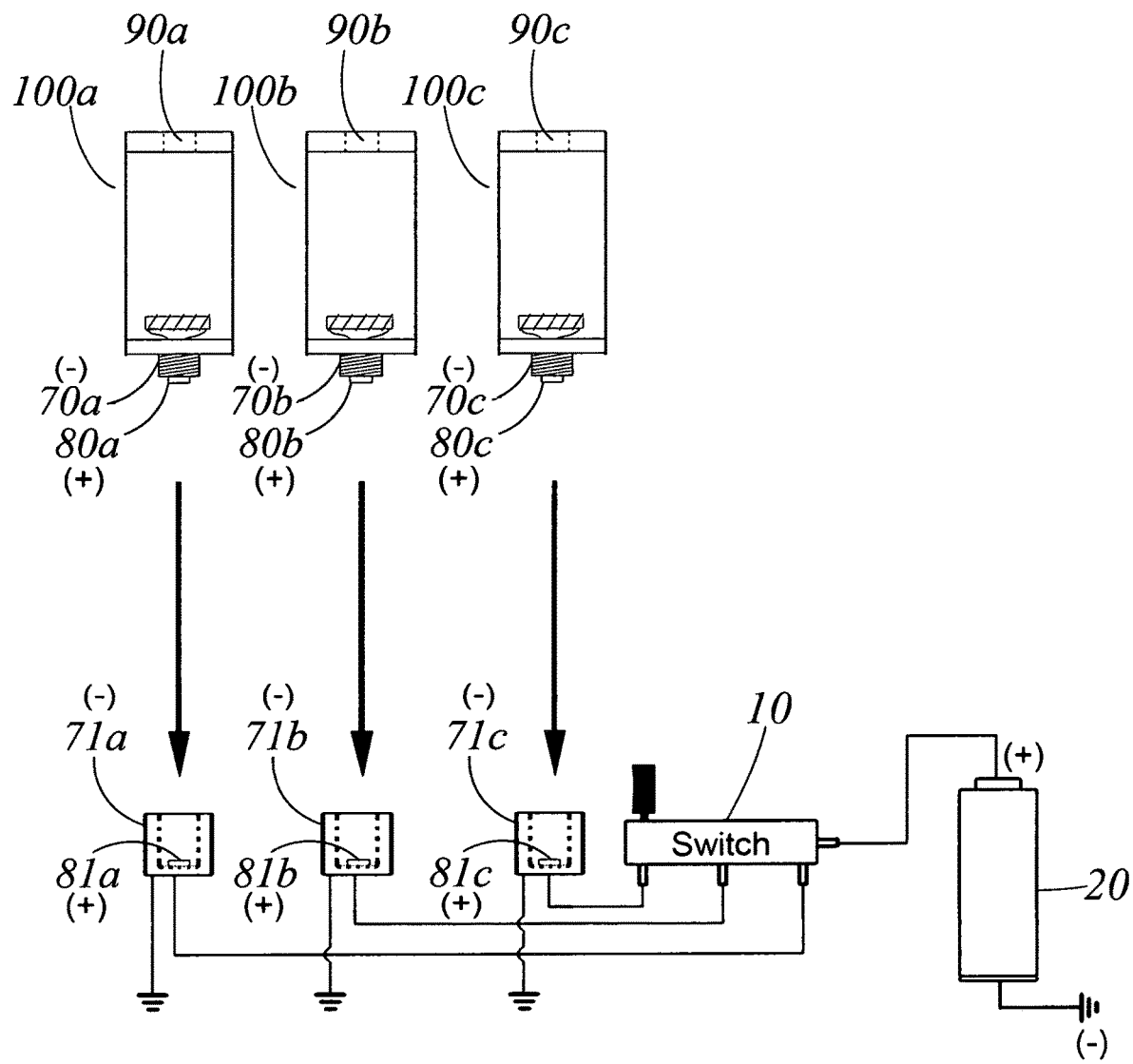
FIG. 10, depicts the same concept and virtually the same system as FIG. 9, but specifically represents the extremely common screw-in cartridge style system with a screw in functionality like that of an Edison light bulb.

FIG. 10, depicts the same concept and virtually the same system as FIG. 9, but specifically represents the extremely common screw-in cartridge style system with a screw in functionality like that of an Edison light bulb. In this depiction, each heating-element is bound inside a separate substance-fillable cavity or cartridge 100a, 100b, 100c with one of each of their two electrode ends being separately bound to the threaded bottom end of their corresponding housings 70a, 70b, 70c. Furthermore, the remaining and unused end of each heating-element will be connected to the positive terminal post 80a, 80b, 80c of its cartridge housing 100a, 100b, 100c. Each positive terminal post 80a, 80b, 80c has a corresponding positive terminal post 81a, 81b, 81c that it can mate with to pass along an electrical current from the electric power source or battery 20. These posts mate together when the threaded end 70a, 70b, 70c of each cartridge 100a, 100b, 100c is inserted and threaded into its threaded receiving mate 71a, 71b, 71c fully until the positive terminal posts 80a, 80b, 80c make good physical contact with their correlating mate posts 81a, 81b, 81c. Once they make good physical contact the negative electrical pathway through the threads of each threaded cartridge end 70a, 70b, 70c and their correlating threaded mate ends 71a, 71b, 71c are also making good electrical contact. When all desired cartridges 100a, 100b, 100c are properly screwed on in the aforementioned manner, this example embodiment of the invented circuit is complete and can be used. Further note inhalation air passages 90a, 90b, 90c at the top of the cartridges 100a, 100b, 100c, which are common industry design of air passages that can then be connected to a mouthpiece embodiment that would allow a user to inhale the substance contents from the separate substance-fillable cavities or cartridges 100a, 100b, 100c. In most cases there are also air intakes. However, that part of the system goes beyond the scope of the novel and innovated contribution herein, but these customizations and enhancements can be designed in many ways by $3^{rd}$ parties for substance-fillable cavities or cartridges 100a, 100b, 100c.

Figure 11:
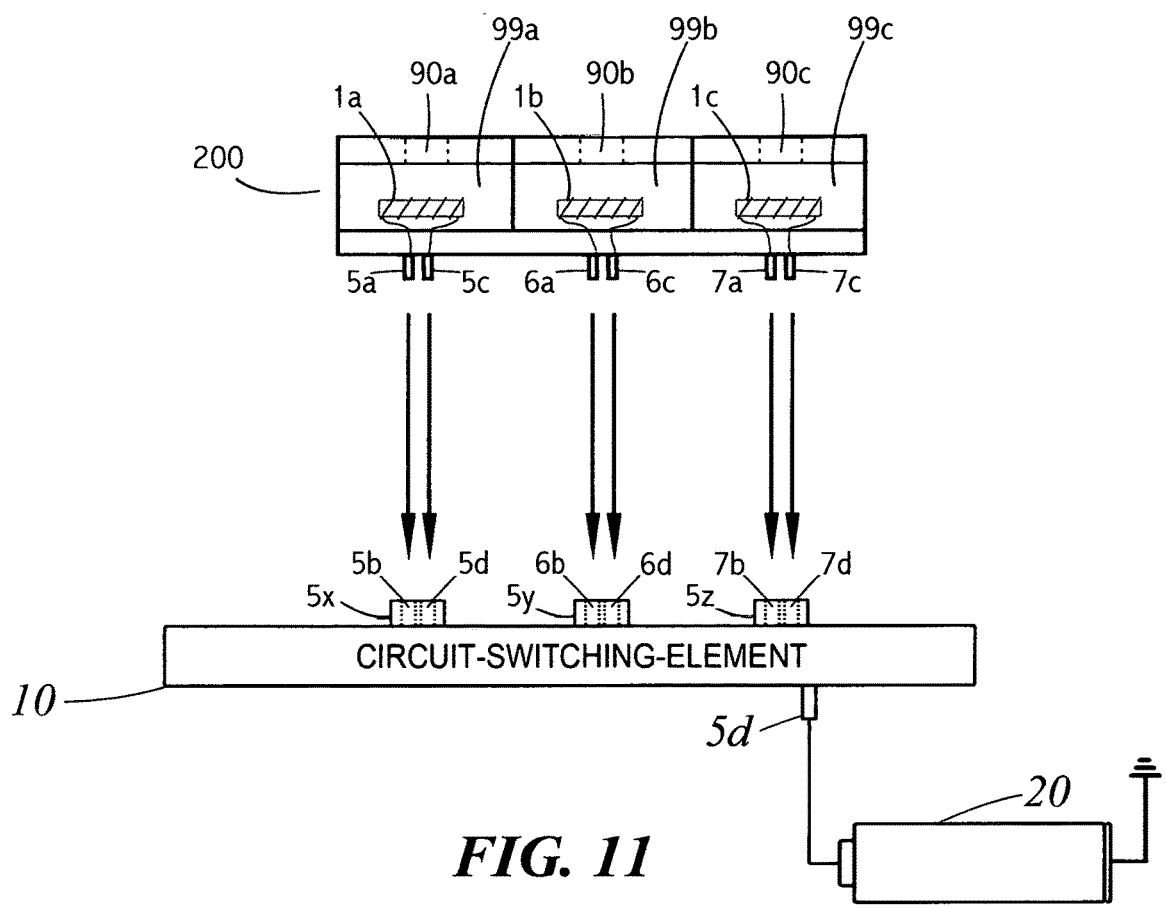
FIG. 11, depicts a press-fit style cartridge and electrical contact system like that shown in FIG. 9, but further shows a single cartridge or shared cavity housing design for inhalable substances that houses 3 heating-elements, each within their own partitioned cavities. Said shared cavity housing system allows a plurality of flavors or strains of inhalable substances to be pre-loaded into 1 cartridge or pod style design.

FIG. 11, depicts a press-fit style shared cavity housing or cartridge 200 and electrical contact system 5x, 5a, 5b, 5c, 5d, 5y, 6a, 6b, 6c, 6d, 5z, 7a, 7b, 7c, 7d like that shown in FIG. 9, but further shows a shared cavity housing 200 housing a plurality of substance-fillable cavities 99a, 99b, 99c for the purpose of housing a plurality of inhalable substances that in this non-limiting example houses three heating-elements 1a, 1b, 1c that are each within their own separate substance-fillable cavities 99a, 99b, 99c. This system allows a user to install one cartridge 200 that they could inhale three different substances from, either one at a time by switching between them or blending them together to varying degrees based on the design of said circuit-switching-element 10. The innovated system herein, may be easily replicated with two-or-more heating-elements in a wide range of fashions. Further note this embodiment shows one of said power source 20 connections going to ground and the other going to the positive input electrode 5d of said circuit-switching-element 10. Additionally, the thru-hole ports 90a, 90b, 90c at the top end of each partitioned cavity 99a, 99b, 99c of said separate substance-fillable cavities or cartridge housing 200 could have a single mouthpiece that collectively fits over them so a user could inhale the substance contents being vaped by any of the three heating-elements 1a, 1b, 1c through a single air intake. As a mouthpiece is arbitrary to the core circuit invention, it can be imagined but is not shown. Lastly depicted in this figure, said circuit-switching-element 10 is shown containing three electrode receptacle housings 5x, 5y, 5z with each one further containing their own female electrical cavities 5b, 5d, 6b, 6d, 7b, 7d for receiving their correlating male electrical mate posts 5a, 5c, 6a, 6c, 7a, 7c from said separate substance-fillable cavities or cartridge housing 200. The pairing pattern for the electrical connections is seen depicted by the arrows in the drawing, indicating each male electrical mate posts 5a, 5c, 6a, 6c, 7a, 7c connects with the electrode receptacle 5b, 5d, 6b, 6d, 7b, 7d directly below it. Note, it is not shown in this depiction how one end of each heating-element is connected to the ground side of the electric power source but is assumed would be easily connected with wires. The main importance of the design in this depiction, is the focus of how the two-or-more heating elements 1a, 1b, 1c could be housed in a one piece removably connectable 3rd party style component 200 and still be operably connectable to said circuit-switching-element 10.

Figure 12:
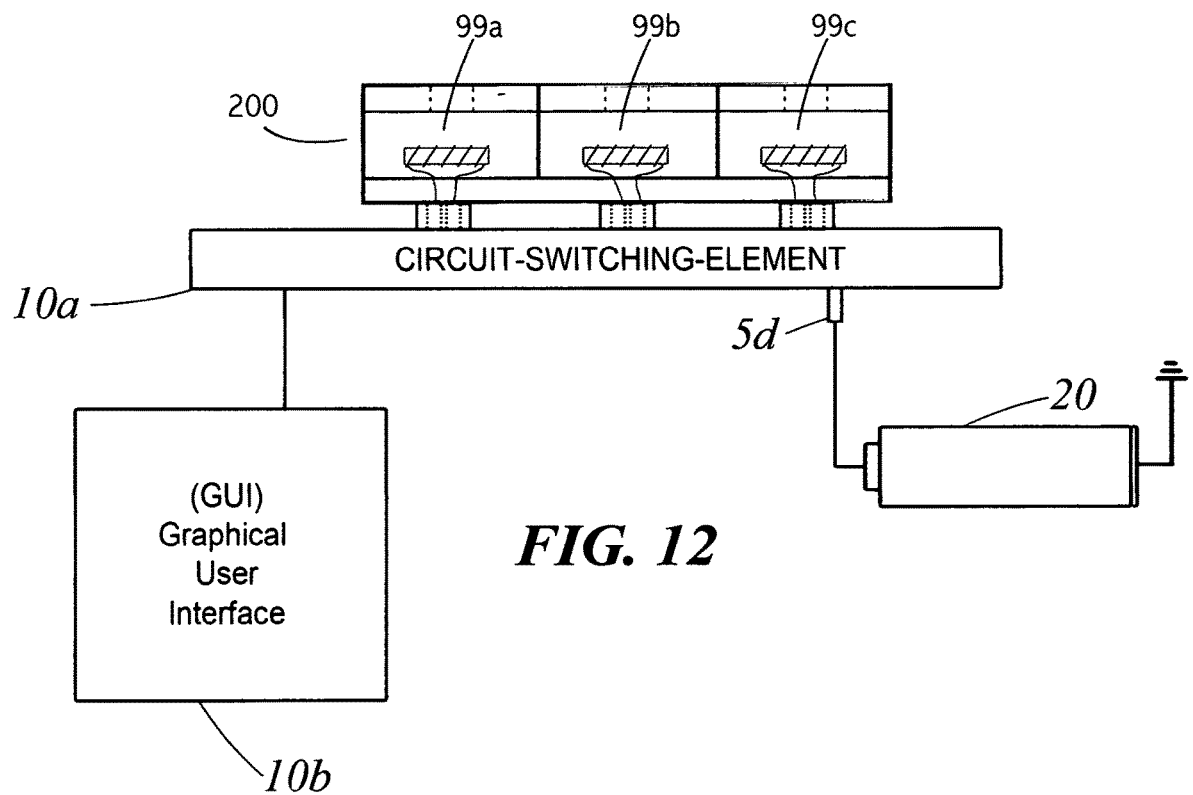
FIG. 12, depicts the same press-fit style cartridge and electrical contact system of that shown in FIG. 11, but additionally shows the removable cartridge containing a shared cavity housing being fully seated and therefore installed into the circuit-switching-element.

FIG. 12, depicts the same press-fit style shared cavity housing or cartridge 200 and electrical contact system of that shown in FIG. 11, but additionally shows the removable cartridge 200 being fully seated and therefore electrically fastened-with and fastened-into said circuit-switching-element 10a. FIG. 12 further depicts a (GUI) Graphical User Interface 10b being operably connected to said circuit-switching-element 10a. With this method, it makes sense to use an (IC) Integrated Circuit as said circuit-switching-element 10a in tandem with said GUI 10b, as their relationship creates an embodiment of the invented circuit that offers the greatest range of use and customization. Furthermore, the two-or-more heating-elements could be housed in a one-piece removably connectable 3$^{rd}$ party style component 200, and still have their electrodes connect with a circuit-switching-element 10a and each still receive power via said electric power source 20 that connects via a positive input electrode 5d on said circuit-switching-element 10a. Lastly, note the partitioned cavities 99a, 99b, 99c of the shared cavity housing or cartridge 200 each house their own heating-element.

FIG. 13, depicts a diagrammatic view of a system in which two-or-more heating-elements 1a, 1b are interfaced with a circuit-switching-element 10 and an electric power source 20, in such a way that their heating abilities may be selectively activated or deactivated by means of user interaction with said circuit-switching-element 10. Further depicted are separate substance-fillable cavities 100a, 100b each housing their own said heating-elements 1a, 1b. The elements and element orientations represented in the drawing herein, encapsulate the most basic structure of the complete invention in its entirety. More heating-elements 1a, 1b can be added to the system herein to increase the systems' versatility and options, but it takes at least two heating-elements 1a, 1b housed inside two separate substance-fillable cavities 100a, 100b, further interfaced to a circuit-switching-element 10 and electric power source 20 to encompass and establish an initial embodiment of the novel invented system herein.

FIG. 14, depicts a diagrammatic view of the same system of FIG. 13 in which two-or-more heating-elements 1a, 1b are interfaced with a circuit-switching-element 10 and an electric power source 20, in such a way that their heating abilities may be selectively activated or deactivated by means of user interaction with said circuit-switching-element 10. Further depicted are separate substance-fillable cavities 99a, 99b each housing their own said heating-elements 1a, 1b. Lastly, a shared cavity housing 200 is depicted wherein the two substance-fillable cavities 99a, 99b are a part of the same material 200 or are unified with an aggregate housing 200. The elements and element orientations represented in the drawing herein, encapsulate the most basic structure of this alternate version of the complete invention in its entirety. More heating-elements 1a, 1b can be added to the system herein to increase the systems versatility and options, but it takes at least two heating-elements 1a, 1b housed inside two separate substance-fillable cavities 100a, 100b, further interfaced to a circuit-switching-element 10 and electric power source 20 to encompass and establish an initial embodiment of the novel invented system herein.

What is claimed is:

1. An electronic system for vaporizing smokable materials for personal inhalation by a user comprising:
    a first heating element for applying heat to a first smokable material to vaporize the first smokable material for inhalation, the first smokable material being contained in a first container;
    a second heating element for applying heat to a second smokable material to vaporize the second smokable material for inhalation, the second smokable material being contained in a second container;
    a power source; and
    a controller to control the multi-heating element circuit switching element, wherein the circuit switching element is selected from the group consisting of a slide switch, one or more push buttons, a rotary encoder, a pressure switch, an infrared switch and a voice activated switch, the circuit switching element to control the first heating element and the second heating element, wherein the controller independently controls the duration and amount of heat for each of the first heating element and second heating element.

2. The electronic system for vaporizing smokable materials for personal inhalation of claim 1 further comprising:
    at least one additional heating element for applying heat to an additional smokable material to vaporize the additional smokable material for inhalation, the additional smokable material contained in an additional container, wherein each additional heating element applies heat to a additional smokable material wherein the additional smokable material is selected from the group consisting of: fluids, oils, juices, waxes, dabs, shatters, distillates, flowers, hashes, tobacco and plant matter;
    and wherein the controller independently controls the duration and amount of heat for each of the additional heating elements.

3. The electronic system for vaporizing smokable materials for personal inhalation of claim 1 wherein the first and second smokable material is selected from the group consisting of: fluids, oils, juices, waxes, dabs, shatters, distillates, flowers, hashes, tobacco and plant matter.

4. The electronic system for vaporizing smokable materials for personal inhalation of claim 1 wherein the first and second materials are different.

5. The electronic system for vaporizing smokable materials for personal inhalation of claim 1 wherein the power source is a battery.

6. The electronic system for vaporizing smokable materials for personal inhalation of claim 1 wherein the first container and second container are a cartridge.

7. The electronic system for vaporizing smokable materials for personal inhalation of claim 6 wherein the cartridges are attached to the vaporizer using a press-fit connection.

8. The electronic system for vaporizing smokable materials for personal inhalation of claim 6 wherein the cartridges are attached to the vaporizer using a screw type connection.

9. The electronic system for vaporizing smokable materials for personal inhalation of claim 6 wherein the cartridges are attached to the vaporizer using a magnetic connection.

* * * * *